US 12,373,964 B2

United States Patent
Zhang et al.

(10) Patent No.: US 12,373,964 B2
(45) Date of Patent: Jul. 29, 2025

(54) METHOD FOR ESTABLISHING NON-RIGID MULTI-MODAL MEDICAL IMAGE REGISTRATION MODEL AND APPLICATION THEREOF

(71) Applicant: Huazhong University of Science and Technology, Hubei (CN)

(72) Inventors: Xuming Zhang, Hubei (CN); Xingxing Zhu, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 396 days.

(21) Appl. No.: 17/997,693

(22) PCT Filed: Apr. 13, 2021

(86) PCT No.: PCT/CN2021/086800
§ 371 (c)(1),
(2) Date: Nov. 1, 2022

(87) PCT Pub. No.: WO2022/205500
PCT Pub. Date: Oct. 6, 2022

(65) Prior Publication Data
US 2023/0316549 A1     Oct. 5, 2023

(30) Foreign Application Priority Data
Mar. 31, 2021   (CN) .......................... 202110345453.8

(51) Int. Cl.
*G06T 7/33*     (2017.01)
*G06T 5/20*     (2006.01)
(Continued)

(52) U.S. Cl.
CPC ............... *G06T 7/337* (2017.01); *G06T 5/20* (2013.01); *G06T 7/344* (2017.01); *G06V 10/454* (2022.01);
(Continued)

(58) Field of Classification Search
CPC .... G06V 20/588; G06V 10/143; G06V 10/24; G06V 10/457; G06V 10/761;
(Continued)

(56) References Cited

U.S. PATENT DOCUMENTS

2020/0184660 A1* 6/2020 Shi ........................... G06T 7/30

FOREIGN PATENT DOCUMENTS

CN     105389775 A *   3/2016
CN     108416802 A     8/2018
(Continued)

OTHER PUBLICATIONS

Wachinger, C, et al. "Entropy and Laplacian images: Structural representations for multi-modal registration." Medical image analysis 16(1): 1-17. 2012. (Year: 2012).*
(Continued)

*Primary Examiner* — Molly Wilburn
*Assistant Examiner* — Emma N. Luke
(74) *Attorney, Agent, or Firm* — HSML P. C.

(57) ABSTRACT

A method for establishing a non-rigid multi-modal medical image registration model includes establishing a generative adversarial network GAN_dr; performing calculation with respect to structural representations of a reference image, a floating image, and an actual registered image in each sample in a medical dataset; using a calculation result to train GAN_dr; establishing a generative adversarial network GAN_ie; using the trained G_dr to generate the deformation recovered structural representations corresponding to each sample in the medical dataset; training GAN_ie; and after connecting the trained G_ie to G_dr, obtaining the registration model.

10 Claims, 4 Drawing Sheets

(51) Int. Cl.
*G06V 10/44* (2022.01)
*G06V 10/74* (2022.01)
*G16H 30/20* (2018.01)

(52) U.S. Cl.
CPC ........... *G06V 10/761* (2022.01); *G16H 30/20* (2018.01); *G06T 2207/20081* (2013.01)

(58) Field of Classification Search
CPC ...... G06V 20/647; G06V 10/30; G06V 10/80; G06V 20/64; G06T 17/00; G06T 2215/16; G06T 7/73; G06T 2207/30256
See application file for complete search history.

(56) References Cited

FOREIGN PATENT DOCUMENTS

| | | |
|---|---|---|
| CN | 110021037 A | 7/2019 |
| CN | 111862174 A | 10/2020 |

OTHER PUBLICATIONS

Huang, J, et al. "MGMDcGAN: medical image fusion using multi-generator multi-discriminator conditional generative adversarial network." IEEE Access 8: 55145-55157. 2020. (Year: 2020).*
International Search Report (with English translation) and Written Opinion issued in PCT/CN2021/086800, dated Dec. 30, 2021, 9 pages provided.

\* cited by examiner

METHOD FOR ESTABLISHING NON-RIGID MULTI-MODAL MEDICAL IMAGE REGISTRATION MODEL AND APPLICATION THEREOF

TECHNICAL FIELD

The present invention pertains to the field of medical image registration, and more particularly, relates to a method for establishing a non-rigid multi-modal medical image registration model and an application thereof.

BACKGROUND ART

Due to different principles of various imaging technology, each imaging method has its own advantages in reflecting human body information. Functional imaging, such as functional magnetic resonance imaging (fMRI), focuses on reflecting human metabolic information, while anatomical imaging, such as T1-weighted MRI, can more clearly reflect the human anatomy. Additionally, even for anatomical imaging such as T1-weighted MRI and T2-weighted MRI, there are differences in information provided thereby. Therefore, fusion of different information from multi-modal images can better assist the diagnosis and treatment of human diseases. Multi-modal medical image registration is the basis of multi-modal medical image information fusion, which is crucial for medical image analysis and clinical research.

Traditional multi-modal medical image registration methods can be roughly divided into two categories: The first category is feature-based registration methods, which extract geometric features of image landmarks and calculate similarity metrics according to the extracted features, and obtain final registered images by means of optimization. However, these methods rely on hand-crafted features, and in the case of large structural differences between multi-modal images, it is difficult to find sufficient corresponding features, and therefore cannot achieve accurate registration. The second category is image grayscale information-based methods. These methods first construct similarity metrics based on the gray-level statistical relationship (such as mutual information or regional mutual information) or correlation (such as a Pearson product-moment correlation) between images, and then optimize an objective function constructed based on the similarity metrics, thereby generating registered images. However, it is difficult for these methods to obtain good registration results when there are large grayscale differences between multi-modal images. Furthermore, the methods ignore local structural information of the images, which easily leads to unsatisfactory registration results in image edge regions. In order to reduce the influence of nonlinear grayscale differences between different modalities, image structural representation methods, such as methods based on entropy images, Weber local descriptor (WLD), modality independent neighborhood descriptor (MIND), and self-similarity context (SSC), are used to characterize image structures to evolve multi-modal image registration into mono-modal image registration, and then the sum of squared differences (SSD) of the structural representations is used as a similarity metrics to implement image registration. Generally, these traditional methods involve time-consuming optimization processes, and therefore it is difficult for these methods to achieve highly efficient medical image registration.

In view of the shortcomings of the above traditional multi-modal image registration methods, in recent years, some researchers have proposed deep learning-based registration methods, which are mainly divided into two categories. The first category is to use deep learning to extract image features, and then construct similarity metrics according to these features, and like traditional methods, use iterative optimization methods to generate registered images, typically represented by PCANet-based registration methods. Although the above methods use features automatically extracted by deep learning methods instead of artificially designed features to implement image registration, such methods still employ iterative optimization strategies to generate registered images, and therefore registration processes thereof are still relatively time-consuming, and it is difficult to achieve highly efficient registration of medical images.

The second category of deep learning-based registration methods is end-to-end image registration methods. These methods use deep learning networks to directly estimate image deformation fields: Hu et al. used a convolutional neural network (CNN) to match anatomical landmarks in a floating image and a reference image, thereby estimating a deformation field; Sokooti et al. used a CNN to learn a deformation field on the basis of multi-dimensional image information and context information; Yang et al. proposed to use a prediction network and a correction network to implement image registration. These registration methods predict a deformation field of an image by using image blocks, while ignore overall information of the image, and are prone to produce discontinuous deformation fields. Balakrishnan et al. proposed a VoxelMorph (Morph)-based image registration method. The method models a registration process of a traditional algorithm, and constructs a loss function using differences between a registered image and a reference image, thereby directly estimating a deformation field between the reference image and a floating image, and uses a spatial conversion layer to apply the deformation field to the floating image to obtain the registered image. Zhao et al. proposed a VTN network consisting of a plurality of cascaded subnetworks for 3D medical image registration; each subnet in the method warps a current floating image, and a registered image is generated at the end of the last subnet. Considering that generative adversarial networks (GAN) can directly generate images through a generative network (G) and a discriminative network (D), GAN-based registration methods are also proposed. These methods utilize a G network to generate a deformation field and warp a floating image to obtain a registration result, and then use the D network to determine whether two images are registered. It is difficult for the above end-to-end deep learning-based image registration methods to effectively deal with nonlinear grayscale differences of multi-modal images, and it is difficult to achieve accurate image registration due to indiscriminate learning of deformations at smooth regions and edge regions.

In general, how to propose an efficient and accurate method for medical image registration is an urgent problem to be solved.

SUMMARY OF THE INVENTION

In view of the defects and improvement requirements of the prior art, the present invention provides a method for establishing a non-rigid multi-modal medical image registration model and an application thereof, the purpose of which is to divide medical image registration into two sub-issues: image deformation recovery and image grayscale estimation, and establish an end-to-end model comprising two stages of generative adversarial networks to achieve fast and accurate matching of medical images.

In order to achieve the above objective, according to one aspect of the present invention, a method for establishing a non-rigid multi-modal medical image registration model is provided, comprising:

obtaining a medical dataset, wherein each sample comprises a pair of reference image and floating image and an actual registered image between these two images;

establishing a first generative adversarial network GAN_dr, wherein a generator G_dr uses structural representations of the reference image and the floating image as an input, to generate a deformation recovered structural representations, and a discriminator D_dr uses the deformation recovered structural representations generated by the generator G_dr and a structural representations of the actual registered image as an input, to determine whether the structural representations generated by the generator G_dr has effectively recovered deformations; performing calculation with respect to the structural representations of the reference image, the floating image, and the actual registered image in each sample in the medical dataset, using a calculation result to train the first generative adversarial network GAN_dr, and upon completion of the training, extracting the generator G_dr therein as a deformation recovery module;

establishing a second generative adversarial network GAN_ie, wherein a generator G_ie uses the structural representations as an input, to estimate a registered image, and a discriminator D_ie uses the registered image estimated by the generator G_ie and the actual registered image as an input, to determine whether the estimated registered image is consistent with the actual registered image; training the second generative adversarial network GAN_ie by using the deformation recovered structural representations corresponding to each sample in the medical dataset generated by the deformation recovery module in combination with the actual registered image corresponding to each sample, and upon completion of the training, extracting the generator G_ie therein as a grayscale estimation module; and after connecting the grayscale estimation module to the deformation recovery module, obtaining a registration model for medical image registration.

According to the present invention, before image registration is performed, the structural representations of the images are calculated first, thereby converting the multi-modal images into mono-modal images, and then registration is performed based on the structural representations, thereby reducing the influence of multi-modality. In the model establishment process, an image registration issue is divided into two sub-issues, namely image deformation recovery and image grayscale estimation. For the image deformation recovery issue, different from existing deep learning methods for estimating an image deformation field, the present invention generates the structural representations of the registered image by using the first-stage generative adversarial network (GAN_dr). In this process, it is possible to focus more on recovery of edge deformations. For the image grayscale estimation, the present invention generates the final grayscale image by inputting the structural representations generated by the first-stage generative adversarial network into the second-stage generative adversarial network (GAN_ie). This process can be regarded as an inverse process of structural representation, and can also focus more on the recovery of edge deformations. The registration model finally established in the present invention is an end-to-end model formed by connecting the generators in the two stages of trained generative adversarial networks. When the model performs image registration, the two stages of generative adversarial networks therein will sequentially perform image deformation recovery and image grayscale estimation, and will focus more on deformations at edge regions, such that final registration results can better focus on deformation recovery of edge regions in the image, reduce the interference from smooth regions, and reach higher registration accuracy. On the other hand, since the registration model established by the present invention is an end-to-end model, a registered image is directly outputted after images to be registered are inputted, without the need for iterative registration, thereby achieving fast and efficient medical image registration.

Further, a calculation formula of the structural representations is:

$$IMIND(I, x) = \exp\left(-\frac{1}{h(x)} \frac{\sum_{m \in M} Dis(I, x, x+m)}{n^2}\right),$$

wherein I represents an image, M represents a spatial search region in the image I, x represents a voxel, and n represents the number of voxels in the spatial search region M; Dis is the sum of squared differences of two image blocks B centered around voxel x and an adjacent voxel x+m thereof in the spatial search region M, $$Dis(I, x_1, x_2) = \sum_{s \in B}(I(x_1 + s) - I(x_2 + s))^2,$$

and $x_1$ and $x_2$ respectively represent two different voxels in the image; h(x) is a decay parameter, $h(x)=(c_1\sigma_1(x)+c_2\sigma_2)^2$; $c_1$ and $c_2$ are constants; $\sigma_1$ and $\sigma_2$ respectively represent a local variance and a global threshold of the image I, $$\sigma_1(x) = \frac{1}{n} \sum_{m \in M} |n \cdot I(x) - I(x+m)|,$$

$\sigma_2$=mean $(\sigma_1(x))$, s.t. $\sigma_1(x) \neq 0$; and mean (•) represents a mean operator.

According to the present invention, when the structural representations of the reference image, the floating image, or the actual registered image is calculated, in the spatial search region, for each voxel, the sum of squared differences Dis of the two image blocks centered around the voxel and the adjacent voxel thereof is calculated, from which local differences of each voxel in respective directions can be obtained, and then all the local differences are fused using the decay parameter to obtain the structural representations. The decay parameter is specifically the square of the weighted sum of the local variance and the global threshold of the image. In the same grayscale set, the decay parameter has a higher response to edge regions, but a lower response to smooth regions. Therefore, the present invention can highlight deformations at the edge regions when using the decay parameter to fuse the local differences, while ensures a small structural difference at the smooth regions, providing clear and complete image representation results, ultimately reducing interference from the smooth regions on the registration results, and further improving image registration accuracy.

Further, the generator G_dr of the first generative adversarial network GAN_dr comprises: two first feature extraction channels, a first feature fusion module, and a first up-sampling module;

the first feature extraction channel comprises N+1 stacked pyramidal convolutional blocks, in which two adjacent pyramidal convolutional blocks are connected by a convolutional layer; the N+1 pyramidal convolutional blocks in the first feature extraction channel are used to extract N+1 features of different scales from an input image; the two first feature extraction channels respectively use the structural representations of the reference image and a structural representations of the input image as inputs, to respectively extract features of different scales from the structural representations of the reference image and the input image; features of the same scale extracted by the two feature extraction channels are subjected to a differential operation by a differential operation layer, to obtain N+1 differential features of different scales;

the first feature fusion module comprises N stacked convolutional-deconvolutional blocks, and the convolutional-deconvolutional blocks are used to perform up-sampling after performing further feature extraction on input features; a cascading layer and a convolutional layer are connected in sequence following each convolutional-deconvolutional block, and an output of the convolutional layer is used as an input of the next convolutional-deconvolutional block or the first up-sampling module; each cascading layer uses a feature outputted by a preceding convolutional-deconvolutional block and a differential feature of a corresponding scale as an input, to perform feature cascading on the input features; the first convolutional-deconvolutional block uses a differential feature of the smallest scale as an input, and each of the remaining convolutional-deconvolutional blocks uses a feature outputted by a preceding convolutional layer as an input;

the first up-sampling module is used to up-sample the input features to a scale consistent with that of the structural representations, to obtain the deformation recovered structural representations, wherein N is a positive integer.

Further, the generator G_ie in the second generative adversarial network GAN_ie comprises: a second feature extraction channel, a second feature fusion module, and a second up-sampling module;

the second feature extraction channel comprises K+1 stacked pyramidal convolutional blocks, in which two adjacent pyramidal convolutional blocks are connected by a convolutional layer; the K+1 pyramidal convolutional blocks in the second feature extraction channel are used to extract K+1 features of different scales from an input image; the second feature extraction channel uses the structural representations as an input, to extract features of different scales from the inputted structural representations;

the second feature fusion module comprises K stacked convolutional-deconvolutional blocks, and the convolutional-deconvolutional blocks are used to perform up-sampling after performing further feature extraction on the input features; a feature addition layer and a convolutional layer are connected in sequence following each convolutional-deconvolutional block, and an output of the convolutional layer is used as an input of the next convolutional-deconvolutional block or the second up-sampling module; each feature addition layer uses a feature outputted by a preceding convolutional-deconvolutional block and a feature of a corresponding scale extracted by the second feature extraction channel as an input, to perform feature addition on the input features; the first convolutional-deconvolutional block uses a feature of the smallest scale extracted by the second feature extraction channel as an input, and each of the remaining convolutional-deconvolutional blocks uses a feature outputted by a preceding convolutional layer as an input;

the second up-sampling module is used to up-sample the input features to a scale consistent with that of the structural representations, to obtain the deformation recovered structural representations, wherein K is a positive integer.

Further, a loss function for training the first generative adversarial network GAN_dr is:

$$L_1 = L_{LSGAN} + \lambda_1 L_{MSE},$$

wherein $\lambda_1$ represents a penalty coefficient, $L_{LSGAN}$ represents a least squares loss, $L_{MSE}$ represents a mean square error between the structural representations generated by the generator G_dr and the structural representations of the actual registered image.

According to the present invention, during the training of the first generation adversarial network GAN_dr, the established loss function comprises both the least squares loss $L_{LSGAN}$ and the mean squared error $L_{MSE}$ between the structural representations generated by the generator G_dr and the structural representations of the actual registered image, wherein the least squares loss $L_{LSGAN}$ can ensure that the generated image has the same data distribution as that of labels (i.e., the actual registered image), and the mean square error $L_{MSE}$ introduced is a penalty function, which can ensure that details of the structural representation are closer to details of the labels.

Further, a loss function for training the second generative adversarial network GAN_ie is:

$$L_2 = L'_{SGAN} + \lambda_2 L_{MSE}' + \lambda_3 (1 - L_{MSSIM}),$$

wherein $\lambda_2$ and $\lambda_3$ represent penalty coefficients, $L'_{LSGAN}$ represents a least squares loss, $L_{MSE}$ represents a mean square error between the registered image estimated by the generator G_ie and the actual registered image, and $L_{MSSIM}$ represents a mean structural similarity between the registered image estimated by the generator G_ie and the actual registered image.

According to the present invention, during the training of the second generation adversarial network GAN_ie, the established loss function comprises all the least squares loss $L_{LSGAN}$, the mean squared error $L_{MSE}$ between the registered image estimated by the generator G_ie and the actual registered image, and the mean structural similarity $L_{MSSIM}$; wherein the least squares loss can ensure that the generated image has the same data distribution as that of the labels (i.e., the actual registered image), the mean square error L'MSE introduced is a penalty function, which can ensure that the details of the structural representation are closer to the details of the labels, and the mean structural similarity $L_{MSSIM}$ introduced can retain more image details.

Further, in the pyramidal convolutional blocks, convolutional kernels of larger sizes are replaced with 3×3×3 dilated convolutional kernels.

According to the present invention, the convolutional kernels of larger sizes, e.g., 5×5×5, 7×7×7, and 9×9×9 convolutional kernels, etc., are replaced with the 3×3×3 dilated convolutional kernels, thereby effectively reducing network parameters and speeding up the training speed of the model.

Further, the discriminator comprises: a plurality of convolutional layers and a fully connected layer connected in sequence, and a batch normalization layer and an LReLU layer are connected in sequence following each convolutional layer, wherein the discriminator is the discriminator D_dr in the first generative adversarial network GAN_dr or the discriminator D_ie in the second generative adversarial network GAN_ie.

According to another aspect of the present invention, a non-rigid multi-modal medical image registration method is provided, comprising:

for a floating image and a reference image to be registered, after respectively performing calculation to obtain structural representations, inputting same into a registration model established by the method for establishing a non-rigid multi-modal medical image registration model provided by the present invention, such that the registration model outputs a registered image.

The non-rigid multi-modal medical image registration method provided by the present invention firstly calculates the structural representations of the reference image and the floating image to be registered, and can convert the multi-modal images into mono-modal images and reduce the influence of multi-modality. On the basis of the registration model established by the present invention, fast and accurate image registration can be achieved, and the non-rigid multi-modal medical image registration method provided by the present invention has a greater registration speed and higher registration accuracy.

According to still another aspect of the present invention, a computer-readable storage medium is provided, comprising a stored computer program, wherein when executed by a processor, the computer program controls a device where the computer-readable storage medium is located to perform the method for establishing a non-rigid multi-modal medical image registration model provided by the present invention, and/or a non-rigid multi-modal medical image registration method provided by the present invention.

In general, by means of the above technical solutions conceived of in the present invention, the following beneficial effects can be achieved:

(1) The present invention divides image registration into two sub-issues: image deformation recovery and image grayscale estimation, and accordingly trains the two stages of generative adversarial networks, in which the generator in the first-stage generative adversarial network generates the structural representations of the registered image, and the generator in the second-stage generative adversarial network generates the final registered image according to the structural representations, in both of which deformation recovery of edge regions can be more focused on, such that the image registration results can better focus on the deformation recovery of the edge regions in the image, and interference from smooth regions is reduced, reaching higher registration accuracy. On the other hand, since the registration model established by the present invention is an end-to-end model, a registered image is directly outputted after images to be registered are inputted, without the need for performing iterative registration, thereby achieving fast and efficient medical image registration. In general, the registration model established by the present invention can achieve efficient and accurate image registration.

(2) According to the present invention, the structural representations of the images are calculated before the image registration is performed, such that the multi-mode images can be converted into mono-modal images and interference of multi-modality can be reduced. In the preferable solutions thereof, when the structural representations of the reference image, the floating image, or the actual registered image is calculated, the local differences of each voxel in respective directions will be calculated first, and then all the local differences will be fused using the decay parameter. Because the calculated decay parameter has a higher response to edge regions, but a lower response to smooth regions, deformations at the edge regions can be highlighted in the fusion process, while a small structural difference at the smooth regions can be ensured, providing clear and complete image representation results, ultimately reducing the interference from the smooth regions on the registration results, and further improving the image registration accuracy.

(3) According to the present invention, during the training of the first generation adversarial network GAN_dr, the established loss function comprises both the least squares loss $L_{LSGAN}$ and the mean squared error $L_{MSE}$ between the structural representations generated by the generator G_dr and the structural representations of the actual registered image, which can ensure that the generated image has the same data distribution as that of the labels (i.e., the actual registered image), and ensure that the details of the structural representation are closer to the details of the labels.

(4) According to the present invention, during the training of the second generation adversarial network GAN_ie, the established loss function comprises all the least squares loss $L'_{LSGAN}$, the mean squared error between the registered image estimated by the generator G_ie and the actual registered image, and the mean structural similarity $L_{MSSIM}$ which can ensure that the generated image has the same data distribution as that of the labels (i.e., the actual registered image), and ensure that the details of the structural representation are closer to the details of the labels, and can retain more image details.

(5) According to the present invention, the convolutional kernels of larger sizes, e.g., 5×5×5, 7×7×7, and 9×9×9 convolutional kernels, etc. are replaced with the 3×3×3 dilated convolutional kernels, thereby effectively reducing network parameters and speeding up the training speed of the model.

DETAILED DESCRIPTION

In order to make the objectives, technical solutions, and advantages of the present invention clearer, the present invention will be further described in detail below with reference to the accompanying drawings and embodiments. It should be understood that the specific embodiments described herein are only intended to explain the present invention, rather than to limit the present invention. In addition, the technical features involved in the various embodiments of the present invention described below can be combined with each other, provided that the technical features do not conflict with each other.

In the present invention, the terms "first", "second", and the like (if any) in the present invention and the accompanying drawings are used to distinguish similar objects, and are not necessarily used to describe a specific order or sequence.

In order to resolve the problems of great time consumption and low efficiency due to registration by iteration, and low image registration accuracy due to blind selection of learning deformations at smooth regions and edge regions of existing non-rigid multi-modal medical image registration methods, the present invention provides a method for establishing a non-rigid multi-modal medical image registration model and an application thereof. The overall idea is to divide medical image registration into two sub-issues: image deformation recovery and image grayscale estimation, and establish an end-to-end model consisting of two stages of generative adversarial networks, in which a generator in the first-stage generative adversarial network is used to implement the image deformation recovery, and a generator in the second-stage generative adversarial network is used to implement the image grayscale estimation, in both of which deformation recovery of edge regions is more focused on, to reduce interference from smooth regions and improve medical image registration accuracy, and the established model directly outputs a registered image according to input images, without the need for performing iteration, thereby improving registration efficiency.

The following are embodiments.

Embodiment 1

Figure 1:
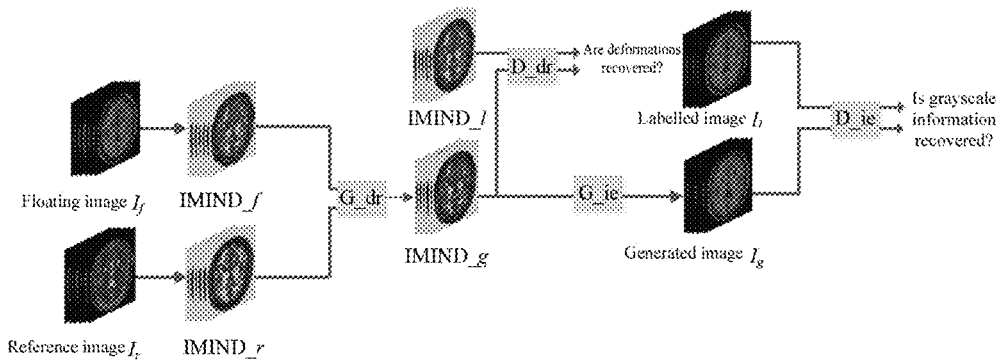
FIG. 1 is a schematic diagram of a method for establishing a non-rigid multi-modal medical image registration model provided by an embodiment of the present invention.

A method for establishing a non-rigid multi-modal medical image registration model, as shown in FIG. 1, comprises the following steps:

(1) Obtain a medical dataset, wherein each sample comprises a pair of reference image and floating image and an actual registered image between these two images.

For ease of expression, the reference image and the floating image in each sample in the medical image dataset are denoted as $I_r$ and $I_f$, respectively. In a subsequent training process, the actual registered image is a labelled image, which is denoted as $I_l$;

(2) Establish a first generative adversarial network GAN_dr, wherein a generator G_dr uses structural representations of the reference image and the floating image as an input, to generate a deformation recovered structural representations, and a discriminator D_dr uses the deformation recovered structural representations generated by the generator G_dr and a structural representations of the actual registered image as an input, to determine whether the structural representations generated by the generator G_dr has effectively recovered deformations; perform calculation with respect to the structural representations of the reference image, the floating image, and the actual registered image in each sample in the medical dataset, use a calculation result to train the first generative adversarial network GAN_dr, and upon completion of the training, extract the generator G_dr therein as a deformation recovery module.

By calculating the structural representations of the images for subsequent image registration, the multi-modal images can be converted into mono-modal images, reducing the interference of multi-modality on registration results.

In order to make a difference in structural representations of corresponding smooth regions in the floating image and the reference image smaller, as an optional implementation manner, in this embodiment, calculation formulas of the structural representations IMIND_r of the reference image $I_r$, the structural representations IMIND_f of the floating image $I_f$, and the structural representations IMIND_l of the labelled image $I_l$ are respectively as follows:

$$\text{IMIND\_r}(I_r, x) = \exp\left(-\frac{1}{h_r(x)} \frac{\sum_{m \in M} Dis(I_r, x, x+m)}{n^2}\right)$$

$$\text{IMIND\_f}(I_f, x) = \exp\left(-\frac{1}{h_f(x)} \frac{\sum_{m \in M} Dis(I_f, x, x+m)}{n^2}\right)$$

$$\text{IMIND\_l}(I_l, x) = \exp\left(-\frac{1}{h_l(x)} \frac{\sum_{m \in M} Dis(I_l, x, x+m)}{n^2}\right)$$

wherein M represents a spatial search region, n represents the number of voxels in the spatial search region M; Dis is the sum of squared differences of two image blocks B centered around the voxel x and an adjacent voxel x+m thereof in M. Calculation formulas of Dis in the reference image $I_r$, the floating image $I_f$, and the labelled image $I_l$ are respectively as follows:

$$Dis(I_r, x_1, x_2) = \sum_{s \in B}(I_r(x_1+s) - I_r(x_2+s))^2$$

-continued $$Dis(I_f, x_1, x_2) = \sum_{s \in B} (I_f(x_1+s) - I_f(x_2+s))^2$$

$$Dis(I_l, x_1, x_2) = \sum_{s \in B} (I_l(x_1+s) - I_l(x_2+s))^2$$

$x_1$ and $x_2$ respectively represent two different voxels in the images; Dis reflects local differences of each voxel in respective directions (and surrounding eight directions thereof), which is a discrete sequence;

$h_r(x)$, $h_f(x)$, and $h_l(x)$ are decay parameters in the reference image $I_r$, the floating image $I_f$, and the labelled image $I_l$, respectively. By using the decay parameters to fuse the local differences of each voxel in the respective directions in the images, continuous structural representations can be obtained. In order to ensure that the decay parameters have a high response to edge regions, but a low response to smooth regions in the same grayscale set, in this embodiment, calculation formulas of the decay parameters are as follows:

$$h_r(x) = (c_1{}^r \sigma_1{}^r(x) + c_2{}^r \sigma_2{}^r)^2$$

$$h_f(x) = (c_1{}^f \sigma_1{}^f(x) + c_2{}^f \sigma_2{}^f)^2$$

$$h_l(x) = (c_1{}^l \sigma_1{}^l(x) + c_2{}^l \sigma_2{}^l)^2$$

wherein $c_1$ and $c_2$ are constants used to ensure that the calculated structural representations can provide clear and complete image representation results. Optionally, in this embodiment, $c_1 = c_2 = 0.8$, $\sigma_1$, and $\sigma_2$ represent a local variance and a global threshold of a corresponding image, respectively, and are defined as follows:

$$\sigma_1^r(x) = \frac{1}{n} \sum_{m \in M} |n \cdot I_r(x) - I_r(x+m)| \quad \sigma_2^r = \text{mean}(\sigma_1^r), \text{ s.t. } \sigma_1^r(x) \neq 0$$

$$\sigma_1^f(x) = \frac{1}{n} \sum_{m \in M} |n \cdot I_f(x) - I_f(x+m)| \quad \sigma_2^f = \text{mean}(\sigma_1^f), \text{ s.t. } \sigma_1^f(x) \neq 0$$

$$\sigma_1^l(x) = \frac{1}{n} \sum_{m \in M} |n \cdot I_l(x) - I_l(x+m)| \quad \sigma_2^l = \text{mean}(\sigma_1^l), \text{ s.t. } \sigma_1^l(x) \neq 0$$

wherein mean(•) represents a mean operator.

In this embodiment, when the structural representations of the images are calculated using the above method, deformations at the edge regions can be highlighted, and a smaller structural difference at the smooth regions can be ensured, providing clear and complete image representation results, and finally reducing the interference from the smooth regions on the registration results, which is beneficial to improving the image registration accuracy.

The structural representations outputted by the generator G_dr is denoted as IMIND_g.

(3) Establish a second generative adversarial network GAN_ie, wherein a generator G_ie uses the structural representations as an input, to estimate a registered image, and a discriminator D_ie uses the registered image estimated by the generator G_ie and the actual registered image as an input, to determine whether the estimated registered image is consistent with the actual registered image; train the second generative adversarial network GAN_ie by using the deformation recovered structural representations corresponding to each sample in the medical dataset generated by the deformation recovery module in combination with the actual registered image corresponding to each sample, and upon completion of the training, extract the generator G_ie therein as a grayscale estimation module.

In this embodiment, the process of generating the final registered image by the generator G_ie in the second generative adversarial network GAN_ie according to the structural representations can be regarded as an inverse process of calculating the structural representations of the image. In this process, the interference from the smooth regions on the registration results can also be reduced, which is beneficial to improving the image registration accuracy.

The registered image estimated by the generator G_ie in the second generative adversarial network GAN_ie is denoted as $I_g$.

(4) After connecting the grayscale estimation module to the deformation recovery module, obtain a registration model for medical image registration.

The registration model established in this embodiment is an end-to-end model, which can directly output a registered image without iteration after a floating image and a reference image to be registered are inputted, achieving a greater registration speed and higher registration efficiency.

Figure 2:
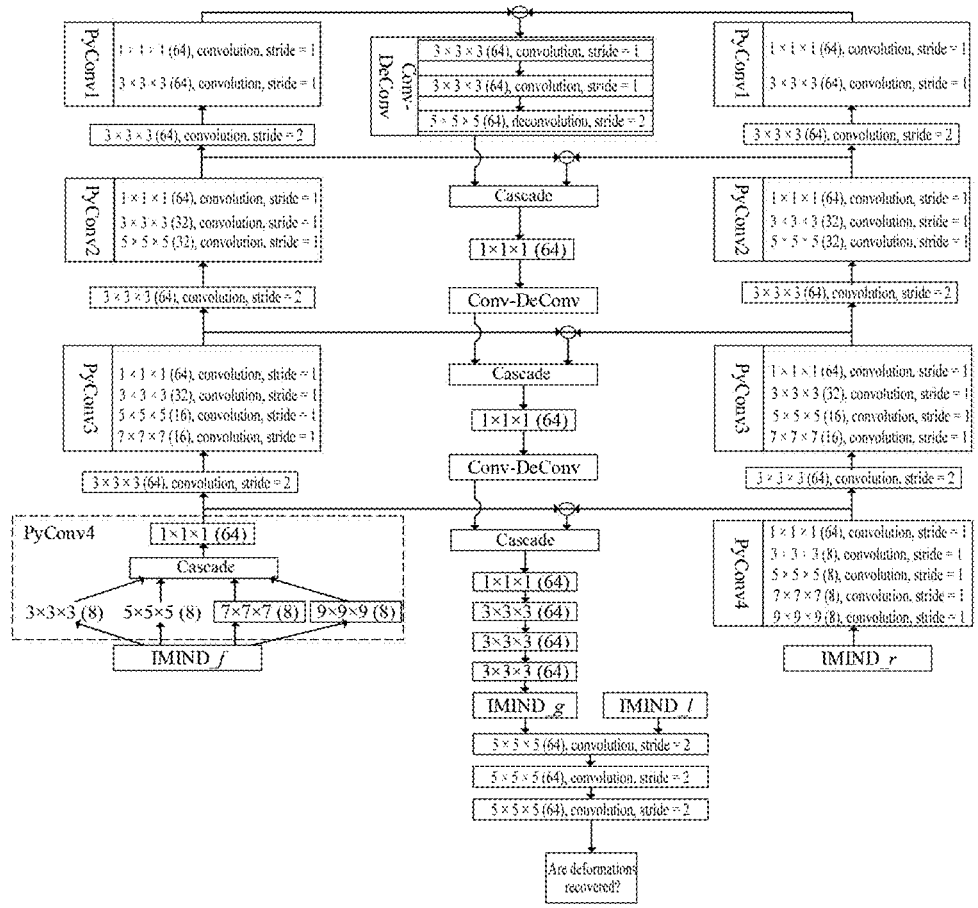
FIG. 2 is a schematic structural diagram of a first generative adversarial network GAN_dr provided by an embodiment of the present invention.

As an optional implementation manner, in this embodiment, the structure of the first generative adversarial network GAN_dr is shown in FIG. 2, wherein the generator G_dr comprises: two first feature extraction channels, a first feature fusion module, and a first up-sampling module.

The first feature extraction channel comprises N+1 stacked pyramidal convolutional blocks, in which two adjacent pyramidal convolutional blocks are connected by a convolutional layer. The N+1 pyramidal convolutional blocks in the first feature extraction channel are used to extract N+1 features of different scales from an input image. The two first feature extraction channels respectively use the structural representations of the reference image and a structural representations of the input image as inputs, to respectively extract features of different scales from the structural representations of the reference image and the input image. Features of the same scale extracted by the two feature extraction channels are subjected to a differential operation by a differential operation layer, to obtain N+1 differential features of different scales.

The first feature fusion module comprises N stacked convolutional-deconvolutional blocks, and the convolutional-deconvolutional blocks are used to perform up-sampling after performing further feature extraction on the input features. A cascading layer and a convolutional layer are connected in sequence following each convolutional-deconvolutional block, and an output of the convolutional layer is used as an input of the next convolutional-deconvolutional block or the first up-sampling module. Each cascading layer uses a feature outputted by a preceding convolutional-deconvolutional block and a differential feature of a corresponding scale as an input, to perform feature cascading on the input features. The first convolutional-deconvolutional block uses a differential feature of the smallest scale as an input, and each of the remaining convolutional-deconvolutional blocks uses a feature outputted by a preceding convolutional layer as an input.

The first up-sampling module is used to up-sample the input features to a scale consistent with that of the structural representations, to obtain the deformation recovered structural representations, wherein N is a positive integer. Optionally, in this embodiment, the specific value of N is 3. Correspondingly, each feature extraction channel comprises four pyramidal convolutional blocks (PyConv), and the feature fusion module comprises three convolutional-deconvolutional blocks (Conv-DeConv), and the four pyramidal convolutional blocks in the same feature extraction channel are respectively denoted as PyConv1 to PyConv4.

PyConv uses convolutional kernels with different sizes to extract information of different sizes of the images. The cascading layers and 1×1×1 the convolutional layers are used to fuse these information to generate features. In order to extract multi-scale features, adjacent PyConv blocks are connected via 3×3×3 convolutional layers with a stride of 2. As the feature scales decrease, the types of convolutional kernels in the PyConv blocks will be reduced. The above process is repeated until there is only one convolutional kernel in the PyConv blocks. The difference between features of two channels of different scales generated by the PyConv blocks will be used by the Conv-DeConv blocks to generate the structural representation of the registered image. Each Conv-DeConv block consists of two convolutional layers with a stride of 1 and one deconvolutional layer (deconv_2) with a stride of 2. The function of deconv_2 is to up-sample the image features to ensure that the generated image has the same size as that of the original image.

For Conv-DeConv, first, the difference between features produced by the last PyConv block is inputted into the first Conv-DeConv block; then, the feature outputted by this Conv-Deconv is fused with a feature generated by the penultimate PyConv block by using a cascading layer and a 1×1×1 convolutional layer, and the fused feature is inputted into the second Conv-Deconv block. The above process is repeated until an output of the last Conv-Deconv block is fused with the feature difference produced by the first PyConv block.

In this embodiment, the discriminator D_dr in the first generative adversarial network GAN_dr comprises: a plurality of convolutional layers and a fully connected layer connected in sequence, and following each convolutional layer, a batch normalization layer and an LReLU layer are connected in sequence. As shown in FIG. 2, specifically, the discriminator D_dr comprises three convolutional layers with a convolutional kernel size of 3×3×3, and following each convolutional layer, a batch normalization layer (BN) and an LReLU layer (leaky rectified linear unit) are used to perform normalization and nonlinear operations on features.

In order to improve the training speed of the model, as an optional implementation manner, in this embodiment, in each PyConv block, convolutional kernels of larger sizes (e.g., 5×5×5, 7×7×7, and 9×9×9 convolutional kernels) are replaced with 3×3×3 dilated convolutional kernels, to reduce the quantity of network parameters.

Figure 3:
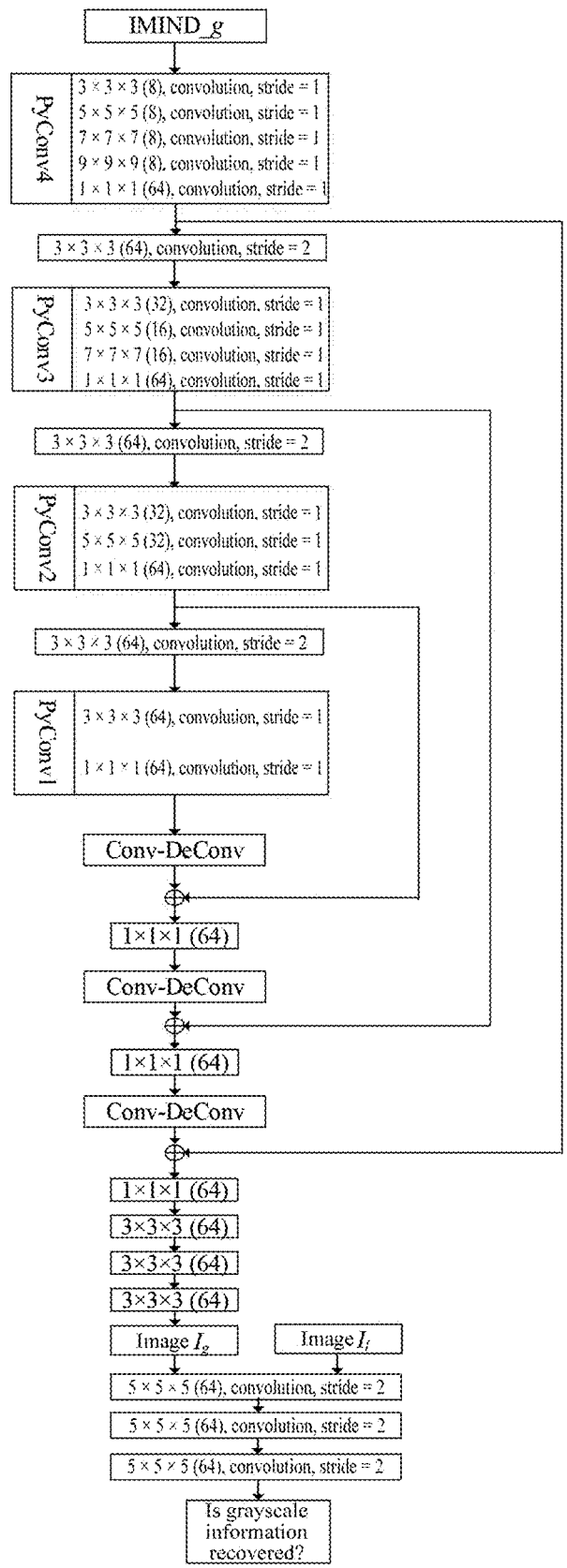
FIG. 3 is a schematic structural diagram of a second generative adversarial network GAN_ie provided by an embodiment of the present invention.

As an optional implementation manner, in this embodiment, the structure of the second generative adversarial network GAN_ie is shown in FIG. 3, wherein the generator G_ie comprises: a second feature extraction channel, a second feature fusion module, and a second sampling module.

The second feature extraction channel comprises K+1 stacked pyramidal convolutional blocks, in which two adjacent pyramidal convolutional blocks are connected by a convolutional layer. The K+1 pyramidal convolutional blocks in the second feature extraction channel are used to extract K+1 features of different scales from an input image. The second feature extraction channel uses the structural representations as an input, to extract features of different scales from the inputted structural representations.

The second feature fusion module comprises K stacked convolutional-deconvolutional blocks, and the convolutional-deconvolutional blocks are used to perform up-sampling after performing further feature extraction on input features. A feature addition layer and a convolutional layer are connected in sequence following each convolutional-deconvolutional block, and an output of the convolutional layer is used as an input of the next convolutional-deconvolutional block or the second up-sampling module. Each feature addition layer uses a feature outputted by a preceding convolutional-deconvolutional block and a feature of a corresponding scale extracted by the second feature extraction channel as an input, to perform feature addition on the input features. The first convolutional-deconvolutional block uses a feature of the smallest scale extracted by the second feature extraction channel as an input, and each of the remaining convolutional-deconvolutional blocks uses a feature outputted by a preceding convolutional layer as an input.

The second up-sampling module is used to up-sample the input features to a scale consistent with that of the structural representations, to obtain the deformation recovered structural representations, wherein K is a positive integer. Optionally, in this embodiment, K=3 is specifically set. Correspondingly, the second feature extraction channel comprises four pyramidal convolutional blocks (PyConv), and the second feature fusion module comprises three convolutional-deconvolutional blocks (Conv-DeConv). As shown in FIG. 3, the four pyramidal convolutional blocks in the second feature extraction channel are respectively denoted as PyConv1 to PyConv4.

In this embodiment, the discriminator D_ie in the second generative adversarial network GAN_ie comprises: a plurality of convolutional layers and a fully connected layer connected in sequence, and following each convolutional layer, a batch normalization layer and an LReLU layer are connected in sequence. As shown in FIG. 3, specifically, the discriminator D_ie comprises three convolutional layers with a convolutional kernel size of 3×3×3, and following each convolutional layer, a batch normalization layer (BN) and an LReLU layer (leaky rectified linear unit) are used to perform normalization and nonlinear operations on features.

Comparing the generative adversarial networks shown in FIG. 2 and FIG. 3, it can be seen that the structure of the discriminator D_ie is the same as that of the discriminator D_dr. The network structure of the generator G_ie is similar to that of the generator G_dr, which is also constructed from the PyConv and Conv-DeConv blocks. The differences between the structures of the generator G_dr and the generator G_ie are that, firstly, the generator G_ie contains only one input channel, while the generator G_dr contains two input channels; secondly, there is not any difference operation after the convolution operation in the generator G_ie; additionally, the generator G_ie uses feature addition to fuse multi-scale information, while the generator G_dr uses feature cascading to fuse multi-scale information.

The first generative adversarial network GAN_dr and the second generative adversarial network GAN_ie are independently trained. The first generative adversarial network GAN_dr is trained first, and the established loss function consists of two parts.

The first part uses a least squares loss function $L_{LSGAN}$, to ensure that the generated image has the same data distribution as that of the labels. The second part introduces the MSE between the generated structural representation IMIND_g and the labels IMIND_l as a penalty function $L_{MSE}$, to ensure that details of the structural representation are closer to details of the labels. The loss function $L_1$ is defined as follows:

$$L_1 = L_{LSGAN} + \lambda_1 L_{MSE}$$

wherein $\lambda_1$ is a penalty coefficient, used to balance $L_{LSGAN}$ and $L_{MSE}$. Optionally, in this embodiment, $\lambda_1=10$;

$L_{LSGAN}$ and $L_{MSE}$ are defined as follows:

$$\min_D L_{LSGAN}(D) = \frac{1}{2}E_{v \sim p_{data}(v)}[(D(v)-1)^2] + \frac{1}{2}E_{z \sim p_z(z)}[(D(G(z)))^2]$$

$$\min_G L_{LSGAN}(G) = \frac{1}{2}E_{z \sim p_2(z)}[(D(G(z))-1)^2]$$

$$L_{MSE} = \frac{1}{Q}\|IMIND\_g - IMIND\_l\|_F^2$$

wherein $\|\cdot\|_F$ represents a Frobenius norm, Q represents the number of voxels in a three-dimensional image, G and D represent the G network and the D network in the first generative adversarial network GAN_dr, respectively.

During the training process, the G network and the D network in GAN_dr are alternately trained until a preset number of iterations (such as 300) is reached, or until a change in the value of the loss function is less than a preset threshold in a preset number of successive iterations (for example, 30 iterations), in which case it is considered that the D network in GAN_dr cannot distinguish whether an input is a generated deformation recovered structural representation or a structural representation of a labelled image.

Upon completion of the training of the first generative adversarial network GAN_dr, the generator therein is used to generate the deformation recovered structural representations corresponding to each sample in the medical image dataset, and then the second generative adversarial network is trained. The established loss function $L_2$ consists of three parts: the first part uses a least squares loss function $L_{LSGAN}'$, to ensure that the generated image has the same data distribution as that of the labels; the second part introduces the MSE between the generated image and the labelled image as a penalty function $L_{MSE}'$; the third part introduces a mean structural similarity (MSSIM) as a penalty function $L_{MSSIM}$, to retain more image details. The loss function $L_2$ is defined as follows:

$$L_2 = L_{LSGAN}' + \lambda_2 L_{MSE}' + \lambda_3 (1 - L_{MSSIM})$$

wherein $\lambda_2$ and $\lambda_3$ are penalty coefficients, used to balance $L_{LSGAN}'$, $L_{MSE}'$, and $L_{MSSIM}$. Optionally, in this embodiment, $\lambda_2=10$, $\lambda_3=1$; $L_{MSE}'$ and $L_{MSSIM}$ are defined as follows:

$$L_{MSE}' = \frac{1}{Q}\|I_g - I_l\|_F^2$$

$$L_{MSSIM} = MSSIM(I_g, I_l) = \frac{1}{j}\sum_{i=1}^{j} SSIM(I_g^i, I_l^i)$$

$$SSIM(I_g^i, I_l^i) = \frac{(2\overline{I_g^i I_l^i} + \varepsilon_1)(2\delta_{I_g^i, I_l^i} + \varepsilon_2)}{(\overline{I_g^i}^2 + \overline{I_l^i}^2 + \varepsilon_1)(\delta_{I_g^i}^2 + \delta_{I_l^i}^2 + \varepsilon_2)}$$

wherein $\overline{I_g^i}$ and $\overline{I_l^i}$ respectively represent the mean values of $I_g^i$ and $I_l^i$; $\varepsilon_1$ and $\varepsilon_2$ are two very small constants used to ensure the stability of SSIM calculation; $S_{I_g^i, I_l^i}$ represents the covariance between $I_g^i$ and $I_l^i$; $\delta_{I_g^i}$ and $\delta_{I_l^i}$ respectively represent the standard deviations of $I_g^i$ and $I_l^i$.

During the training process, an Adam optimizer and a BP algorithm are used to iteratively optimize the GAN_ie network, and alternately train the G network and the D network in GAN_ie, until a preset number of iterations (for example, 300 times) is reached, or until a change in the value of the loss function $L_2$ is smaller than a preset threshold in a preset number (e.g., 30) of successive iterations, in which case it is considered that the D network in GAN_ie cannot discriminate whether an input is an estimated registered image or an actual registered image.

In general, the above technical solution proposed in this embodiment has the following advantages compared with existing registration methods. First, compared with the traditional registration methods, this method employs deep learning to achieve end-to-end non-rigid registration of medical images, and directly estimates registered images, rather than generating registration results by using an iterative method, thereby achieving fast and efficient medical image registration. Second, compared with the existing deep learning methods for registration, this method divides a registration issue into two sub-issues: image deformation recovery and image grayscale estimation. For the image deformation recovery, different from the existing deep learning methods for estimating an image deformation field, we use a GAN network to generate a structural representations of a registered image. Because the difference between structural representations of corresponding smooth regions between a reference image and the registration result is very small, the method proposed in this patent enables the network to focus on recovery of deformations at edge regions. For the image grayscale estimation, we regard the process as an inverse process of structural representation, and generate a final grayscale image by inputting the structural representations generated by the first-stage GAN. Overall, the method proposed in this patent divides the registration issue into two sub-issues, and can better focus on the deformation recovery at the edge regions in the image, reduce the interference from smooth regions, and has higher registration accuracy than the existing methods.

Embodiment 2

Figure 4:
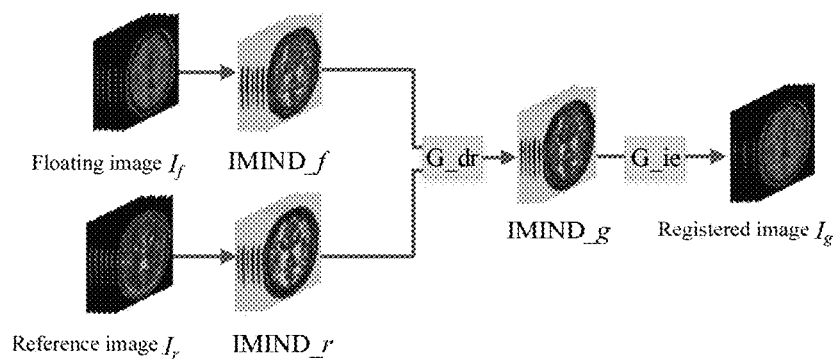
FIG. 4 is a schematic diagram of a non-rigid multi-modal medical image registration method provided by an embodiment of the present invention.

A non-rigid multi-modal medical image registration method, as shown in FIG. 4, comprises:

For a floating image $I_f$ and a reference image $I_r$ to be registered, after structural representations IMIND_f and IMIND_r are calculated respectively, the calculated structural representations are inputted into the registration model established according to the method for establishing a non-rigid multi-modal medical image registration model provided by the above Embodiment 1, to output a registered image $I_g$ from the registration model.

According to the non-rigid multi-modal medical image registration method provided by this embodiment, the structural representations of the reference image and the floating image to be registered are calculated first, such that the multi-modal images can be converted into mono-modal images, reducing the influence of multi-modality. Based on the registration model established in this embodiment, fast and accurate image registration can be achieved. The non-rigid multi-modal medical image registration method provided in this embodiment has a greater registration speed and higher registration accuracy.

Embodiment 3

A computer-readable storage medium comprises a stored computer program. When the computer program is executed by a processor, a device where the computer-readable storage medium is located is controlled to perform the method for establishing a non-rigid multi-modal medical image registration model provided in the above Embodiment 1, and/or the non-rigid multi-modal medical image registration method provided in the above Embodiment 2.

Registration effects of the present invention will be further explained below in conjunction with comparative experimental results. During the experiment, five existing registration methods are selected as comparative embodiments of the above Embodiment 2, and the comparative embodiments are as follows:

Comparative Embodiment 1

Registration was implemented according to the VTN method in (IEEE J BIOMED HEALTH. 24 (5) (2019) 1394-1404), and specific parameters were: a batch size during training was 2, a learning rate was 0.0001, and a momentum was 0.5;

Comparative Embodiment 2

Registration was implemented according to the morph method in (CVPR. 2018, pp. 9252-9260), and specific parameters were: a batch size during training was 2, a learning rate was 0.0001, and a momentum was 0.5.

Comparative Embodiment 3

Registration was implemented according to the SSC method in (MICCAI. 2013, pp. 187-194), and specific parameters were: an image block size was 3×3.

Comparative Embodiment 4

Registration was implemented according to the MIND method in (Med. Image Anal. 16 (7) (2012). 1423-1435), and specific parameters were: an image block size was 3×3.

Comparative Embodiment 5

Registration was implemented according to the ESSD method in (Med. Image Anal. 16 (1) (2012) 1-17). Specific parameters were: 9×9 image blocks were selected, and Gaussian weights, a local normalization method, and Parzen window estimation were employed to calculate an entropy corresponding to the image blocks, thereby obtaining an ESSD corresponding to an entire image.

The registration accuracy was evaluated using a dice value, wherein dice was defined as:

$$Dice = \frac{2|A \cap B|}{|A| + |B|}$$

wherein |A| represents the number of voxels in image A, |B| represents the number of voxels in image B, and |A∩B| represents the number of voxels in a common part of image A and image B.

In a comparative experiment, simulated MR images were used to test registration accuracy. Simulated T1 and T2-weighted MR images used were taken from a BrainWeb database, wherein T1 was a floating image, as shown by (a) in FIGS. 5, and T2 was a reference image, as shown by (b) in FIG. 5. During the experiment, a 3D-slicer was used to segment white matter, gray matter, and cerebrospinal fluid (CSF) in a registered image and the reference image, and dice values thereof were calculated to determine registration accuracy. Table 1 lists the standard deviation and mean of the dice value of each part obtained by each registration method. It can be seen from Table 1 that when multi-modal MR images were registered, the mean value of the dice value provided in Embodiment 2 was higher than those of the other methods, and the standard deviation was lower than those of the other methods, which indicates that the method proposed in the present invention has the highest registration accuracy among all the methods compared.

Figure 5:
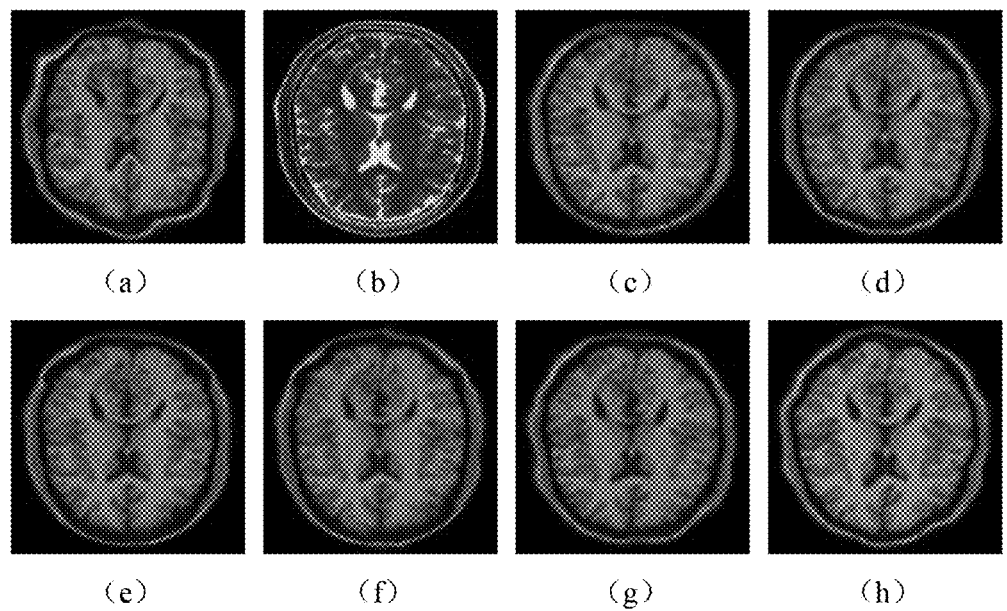
FIG. 5 is a schematic diagram of registration results of performing registration on a floating image T1 and a reference image T2 by different registration methods provided by embodiments of the present invention, wherein (a) is the floating image T1, (b) is the reference image T2, (c) is the T1-T2 image registration result obtained by an embodiment of the present invention; (d) is the T1-T2 image registration result obtained by the method in Comparative Embodiment 1; (e) is the T1-T2 image registration result obtained by the method in Comparative Embodiment 2; (f) is the T1-T2 image registration result obtained by the method in Comparative Embodiment 3; (g) is the T1-T2 image registration result obtained by the method in Comparative Embodiment 4; (h) is the T1-T2 image registration result obtained by the method in Comparative Embodiment 5.

The registration results of the floating image T1 and the reference image T2 in Embodiment 2 and Comparative Embodiments 1-5 are respectively shown in (c) to (h) in FIG. 5, wherein (c) is the T1-T2 image registration result obtained by the method in Embodiment 2 of the present invention; (d) is the T1-T2 image registration result obtained by the method in Comparative Embodiment 1; (e) is the T1-T2 image registration result obtained by the method in Comparative Embodiment 2; (f) is the T1-T2 image registration result obtained by the method in Comparative Embodiment 3; (g) is the T1-T2 image registration result obtained by the method in Comparative Embodiment 4; (h) is the T1-T2 image registration result obtained by the method in Comparative Embodiment 5. It can be seen from the registration result diagram that the method in Embodiment 2 of the present invention could better recover deformations at edge regions, and therefore obtained better registration results than those of the other comparative embodiments, which indicates that the registration method provided by the present invention can obtain higher registration accuracy.

TABLE 1

Comparison of dice values of methods during T1-T2 image registration

| | Dice value | | | | | | | |
|---|---|---|---|---|---|---|---|---|
| | White matter | | Gray matter | | CSF | | | |
| Registration method | Mean | Standard deviation | Mean | Standard deviation | Mean | Standard deviation | Mean | Standard deviation |
| Embodiment | 0.86 | 0.026 | 0.82 | 0.024 | 0.84 | 0.042 | 0.84 | 0.034 |
| Comparative Embodiment 1 | 0.83 | 0.036 | 0.79 | 0.031 | 0.81 | 0.062 | 0.81 | 0.054 |
| Comparative Embodiment 2 | 0.83 | 0.035 | 0.78 | 0.031 | 0.79 | 0.057 | 0.80 | 0.048 |
| Comparative Embodiment 3 | 0.81 | 0.043 | 0.75 | 0.053 | 0.80 | 0.061 | 0.78 | 0.053 |
| Comparative Embodiment 4 | 0.77 | 0.051 | 0.73 | 0.056 | 0.77 | 0.065 | 0.76 | 0.055 |
| Comparative Embodiment 5 | 0.70 | 0.048 | 0.68 | 0.057 | 0.69 | 0.073 | 0.69 | 0.067 |

Figure 6:
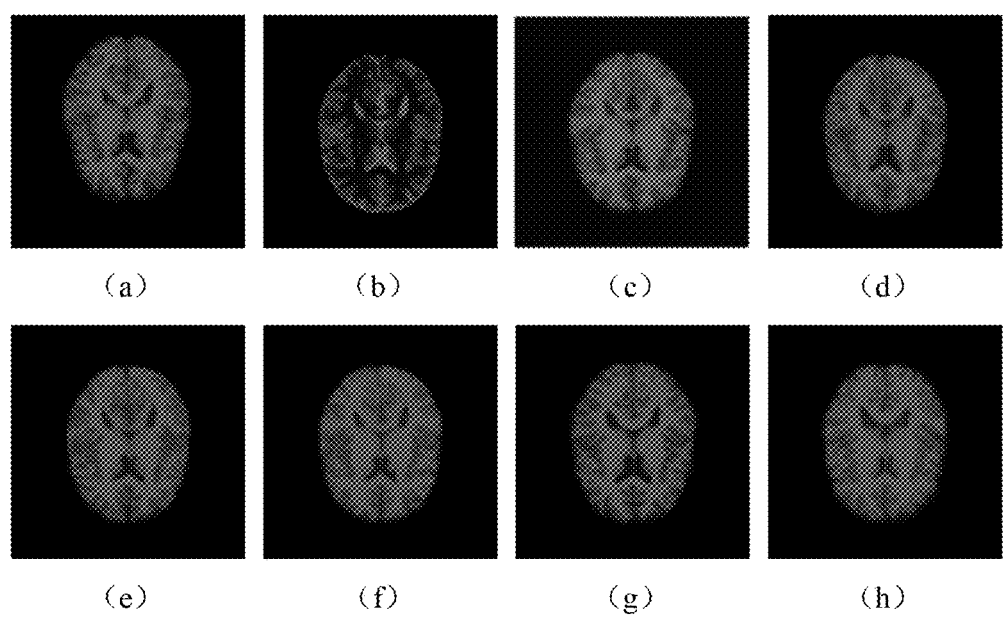
FIG. 6 is a schematic diagram of registration results of performing registration on a floating image T1 and a reference image PD by different registration methods provided in embodiments of the present invention, wherein (a) is the floating image T1, (b) is the reference image PD, (c) is the T1-PD image registration result obtained by the method of an embodiment of the present invention; (d) is the T1-PD image registration result obtained by the method in Comparative Embodiment 1; (e) is the T1-PD image registration result obtained by the method in Comparative Embodiment 2; (f) is the T1-PD image registration result obtained by the method in Comparative Embodiment 3; (g) is the T1-PD image registration result obtained by the method in Comparative Embodiment 4; (h) is the T1-PD image registration result obtained by the method in Comparative Embodiment 5.

In another comparative experiment, MR images in an IXI dataset and a BrainWeb dataset were used to implement image-dataset registration. The BrainWeb dataset, which simulates MR brain images, was used as reference images, and medical images in the IXI dataset were used as floating images. The used floating image T1 is shown in FIG. 6(a), and the used reference image PD is shown in FIG. 6(b). Registration results of registering the floating image T1 and the reference image PD in Embodiment 2 and Comparative Embodiments 1-5 are shown in (c) to (h) in FIG. 6, respectively, wherein (c) is the T1-PD image registration result obtained in Embodiment 2 of the present invention; (d) is the T1-PD image registration result obtained by the method in Comparative Embodiment 1; (e) is the T1-PD image registration result obtained by the method in Comparative Embodiment 2; (f) is the T1-PD image registration result obtained by the method in Comparative Embodiment 3; (g) is the T1-PD image registration result obtained by the method in Comparative Embodiment 4; and (h) is the T1-PD image registration result obtained by the method in Comparative Embodiment 5. From the registration results shown in FIG. 6, it can be seen that Comparative Embodiment 5 did not perform well in recovering deformations of the contour and the internal structure, and the methods of Comparative Embodiments 1-4 outperformed that of Comparative Embodiment 5, but the methods could not effectively recover deformations at some structurally complex regions. In contrast, the method of Embodiment 2 of the present invention could better recover deformations at edge regions, such that a good registered image could be obtained.

In the experiment, 3D-slicer was first used to segment the white matter, gray matter, and cerebrospinal fluid (CSF) in the registered image and the reference image, and the dice values thereof were calculated to determine registration accuracy. Table 2 shows the standard deviation and mean of the dice value of each part obtained by each algorithm.

TABLE 2

Comparison of dice values of methods in T1-PD image registration

| Registration method | Dice value | | | | | | | |
|---|---|---|---|---|---|---|---|---|
| | White matter | | Gray matter | | CSF | | | |
| | Mean | standard deviation | Mean | Standard deviation | Mean | Standard deviation | Mean | Standard deviation |
| Embodiment | 0.83 | 0.034 | 0.82 | 0.029 | 0.86 | 0.037 | 0.83 | 0.045 |
| Comparative Embodiment 1 | 0.78 | 0.040 | 0.79 | 0.039 | 0.77 | 0.061 | 0.78 | 0.058 |
| Comparative Embodiment 2 | 0.79 | 0.045 | 0.77 | 0.033 | 0.80 | 0.058 | 0.78 | 0.054 |
| Comparative Embodiment 3 | 0.74 | 0.051 | 0.76 | 0.062 | 0.75 | 0.067 | 0.75 | 0.072 |
| Comparative Embodiment 4 | 0.73 | 0.062 | 0.69 | 0.064 | 0.73 | 0.078 | 0.72 | 0.073 |
| Comparative Embodiment 5 | 0.64 | 0.081 | 0.64 | 0.069 | 0.67 | 0.092 | 0.65 | 0.084 |

It can be seen from the results shown in Table 2 that, compared with other registration methods, the method in Embodiment 2 of the present invention could obtain a higher average dice value for image-dataset registration, and had a lower standard deviation. This shows that the registration method proposed in the present invention has higher registration accuracy in image-dataset image registration than the algorithms of the comparative embodiments.

Those skilled in the art could easily understand that described above are only preferred embodiments of the present invention, and are not intended to limit the present invention. Any modifications, equivalent replacements, and improvements made within the spirit and principles of the present invention, etc., should all be comprised within the scope of protection of the present invention.

The invention claimed is:

1. A method for establishing a non-rigid multi-modal medical image registration model, comprising:

obtaining a medical dataset, wherein each sample comprises a pair of reference image and floating image and an actual registered image between the reference image and the floating image;

establishing a first generative adversarial network GAN_dr, wherein a generator G_dr uses structural representations of the reference image and the floating image as a first input, to generate a deformation recovered structural representations, and a discriminator D_dr uses the deformation recovered structural representations generated by the generator G_dr and a structural representations of the actual registered image as a second input, to determine whether the structural representations generated by the generator G_dr has effectively recovered deformations; performing calculation with respect to the structural representations of the reference image, the floating image, and the actual registered image in each sample in the medical dataset, using a calculation result to train the first generative adversarial network GAN_dr, and upon completion of the training, extracting the generator G_dr therein as a deformation recovery module;

establishing a second generative adversarial network GAN_ie, wherein a generator G_ie uses the deformation recovered structural representations as a third input, to estimate a registered image, and a discriminator D_ie uses the registered image estimated by the generator G_ie and the actual registered image as a fourth input, to determine whether the estimated registered image is consistent with the actual registered image; training the second generative adversarial network GAN_ie by using the deformation recovered structural representations corresponding to each sample in the medical dataset generated by the deformation recovery module in combination with the actual registered image corresponding to each sample, and upon completion of the training, extracting the generator G_ie therein as a grayscale estimation module; and after connecting the grayscale estimation module to the deformation recovery module, obtaining a registration model for medical image registration.

2. The method for establishing a non-rigid multi-modal medical image registration model according to claim 1, wherein a calculation formula of the structural representations is:

$$(I, x) = \exp\left(-\frac{1}{h(x)} \frac{\sum_{m \in M} Dis(I, x, x+m)}{n^2}\right); \quad \text{(I1x)}$$

wherein I represents an image, M represents a spatial search region in the image I, m is a member of M, x represents a voxel, and n represents the number of voxels in the spatial search region M; Dis is the sum of squared differences of two image blocks B centered around voxel x and an adjacent voxel x+m thereof in the spatial search region M, s is a member of B, $$Dis(I, x_1, x_2) = \sum_{s \in B}(I(x_1+s) - I(x_2+s))^2,$$

and $x_1$ and $x_2$ respectively represent two different voxels in the image; h(x) is a decay parameter, $h(x) = (c_1\sigma_1(x) + c_2\sigma_2)^2$; $c_1$ and $c_2$ are constants; $\sigma_1$ and $\sigma_2$ respectively represent a local variance and a global threshold of the image I, $$\sigma_1(x) = \frac{1}{n}\sum_{m \in M}|n \cdot I(x) - I(x+m)|,$$

$\sigma_2 = \text{mean}(\sigma_1(x))$, s.t. $\sigma_1(x) \neq 0$; and mean(•) represents a mean operator.

3. The method for establishing a non-rigid multi-modal medical image registration model according to claim 1, wherein the generator G_dr of the first generative adversarial network GAN_dr comprises: two first feature extraction channels, a first feature fusion module, and a first up-sampling module;

each of the two first feature extraction channels comprises N+1 stacked pyramidal convolutional blocks, in which two adjacent blocks of the N+1 stacked pyramidal convolutional blocks are connected by a first convolutional layer; the N+1 stacked pyramidal convolutional blocks in the each of the two first feature extraction channels are used to extract N+1 features of different scales from an input image; the two first feature extraction channels respectively use the structural representations of the reference image and a structural representations of the input image as inputs, to respectively extract features of different scales from the structural representations of the reference image and the input image; features of the same scale extracted by the two first feature extraction channels are subjected to a differential operation by a differential operation layer, to obtain N+1 differential features of different scales;

the first feature fusion module comprises N stacked convolutional-deconvolutional blocks, and the N stacked convolutional-deconvolutional blocks are used to perform up-sampling after performing further feature extraction on input features; a cascading layer and a second convolutional layer are connected in sequence following each of the N stacked convolutional-deconvolutional blocks, and an output of the convolutional layer is used as an input of a next block of the N stacked convolutional-deconvolutional blocks or the first up-sampling module; each cascading layer uses a first feature outputted by a preceding convolutional-deconvolutional block and a differential feature of a corresponding scale as a fifth input, to perform feature cascading on the input features; a first block of the N stacked convolutional-deconvolutional blocks uses a differential feature of the smallest scale as a sixth input, and each of remaining N stacked convolutional-deconvolutional blocks uses a second feature outputted by a preceding convolutional layer as a seventh input; and the first up-sampling module is used to up-sample the input features to a scale consistent with that of the structural representations, to obtain the deformation recovered structural representations, wherein N is a positive integer.

4. The method for establishing a non-rigid multi-modal medical image registration model according to claim 3, wherein the generator G_ie in the second generative adversarial network GAN_ie comprises: a second feature extraction channel, a second feature fusion module, and a second up-sampling module;

the second feature extraction channel comprises K+1 stacked pyramidal convolutional blocks, in which two adjacent blocks of the K+1 stacked pyramidal convolutional blocks are connected by a third convolutional layer; the K+1 stacked pyramidal convolutional blocks in the second feature extraction channel are used to extract K+1 features of different scales from the input image; the second feature extraction channel uses the structural representations as an eighth input, to extract features of different scales from the inputted structural representations;

the second feature fusion module comprises K stacked convolutional-deconvolutional blocks, and the K stacked convolutional-deconvolutional blocks are used to perform up-sampling after performing further feature extraction on input features; a feature addition layer and a fourth convolutional layer are connected in sequence following each of the K stacked convolutional-deconvolutional blocks, and an output of the convolutional layer is used as an input of a next block of the K stacked convolutional-deconvolutional blocks or the second up-sampling module; each feature addition layer uses a third feature outputted by a preceding convolutional-deconvolutional block and a feature of a corresponding scale extracted by the second feature extraction channel as a ninth input, to perform feature addition on the input features; a first block of the K stacked convolutional-deconvolutional block uses a feature of the smallest scale extracted by the second feature extraction channel as a tenth input, and each of remaining K stacked convolutional-deconvolutional blocks uses a fourth feature outputted by a preceding convolutional layer as an eleventh input; and the second up-sampling module is used to up-sample the input features to a scale consistent with that of the structural representations, to obtain the deformation recovered structural representations, wherein K is a positive integer.

5. The method for establishing a non-rigid multi-modal medical image registration model according to claim 1, wherein a loss function for training the first generative adversarial network GAN_dr is:

$$L_1 = L_{LSGAN} + \lambda_1 L_{MSE},$$

wherein $\lambda_1$ represents a penalty coefficient, $L_{LSGAN}$ represents a least squares loss, $L_{MSE}$ represents a mean square error between the structural representations generated by the generator G_dr and the structural representations of the actual registered image.

6. The method for establishing a non-rigid multi-modal medical image registration model according to claim 1, wherein a loss function for training the second generative adversarial network GAN_ie is:

$$L_2 = L_{LSGAN}' + \lambda_2 L_{MSE}' + \lambda_3 (1 - L_{MSSIM}),$$

wherein $\lambda_2$ and $\lambda_3$ represent penalty coefficients, $L_{LSGAN}'$ represents a least squares loss, $L_{MSE}'$ represents a mean square error between the registered image estimated by the generator G_ie and the actual registered image, and $L_{MSSIM}$ represents a mean structural similarity between the registered image estimated by the generator G_ie and the actual registered image.

7. The method for establishing a non-rigid multi-modal medical image registration model according to claim 3, wherein in the N+1 stacked pyramidal convolutional blocks, convolutional kernels of larger sizes are replaced with 3×3×3 dilated convolutional kernels.

8. The method for establishing a non-rigid multi-modal medical image registration model according to claim 3, wherein the discriminator comprises: a plurality of convolutional layers and a fully connected layer connected in sequence, and a batch normalization layer and an LReLU layer are connected in sequence following each convolutional layer, wherein the discriminator is the discriminator D_dr in the first generative adversarial network GAN_dr or the discriminator D_ie in the second generative adversarial network GAN_ie.

9. A non-rigid multi-modal medical image registration method, comprising:

for the floating image of claim 1 to be registered and the reference image of claim 1, after respectively performing calculation to obtain structural representations of the floating image and the reference image, inputting the structural representations of the floating image and the reference image into the registration model of claim 1 established by the method for establishing the non-rigid multi-modal medical image registration model according to claim 1, such that the registration model outputs the registered image of claim 1.

10. A non-transitory computer-readable storage medium, comprising a computer program stored in the non-transitory computer-readable storage medium, wherein when executed by a processor, the computer program controls a device where the non-transitory computer-readable storage medium is located to perform the method for establishing the non-rigid multi-modal medical image registration model according to claim 1.

* * * * *